United States Patent
Dahl

(10) Patent No.: US 9,981,854 B2
(45) Date of Patent: May 29, 2018

(54) PROCESS FOR CO-PRODUCTION OF AMMONIA, UREA AND METHANOL

(71) Applicant: Haldor Topsøe, Kgs. Lyngby (DK)

(72) Inventor: Per Juul Dahl, Vedbæk (DK)

(73) Assignee: Haldor Topsoe A/S, Lyngby (DK)

( * ) Notice: Subject to any disclaimer, the term of this patent is extended or adjusted under 35 U.S.C. 154(b) by 129 days.

(21) Appl. No.: 14/787,797

(22) PCT Filed: Apr. 16, 2014

(86) PCT No.: PCT/EP2014/057765
§ 371 (c)(1),
(2) Date: Oct. 29, 2015

(87) PCT Pub. No.: WO2014/187621
PCT Pub. Date: Nov. 27, 2014

(65) Prior Publication Data
US 2016/0083260 A1    Mar. 24, 2016

(30) Foreign Application Priority Data

May 23, 2013  (EP) ..................................... 13168896

(51) Int. Cl.
| | |
|---|---|
| *C01C 1/04* | (2006.01) |
| *C01B 3/02* | (2006.01) |
| *C01B 3/38* | (2006.01) |
| *C01B 3/48* | (2006.01) |
| *C07C 273/04* | (2006.01) |

(Continued)

(52) U.S. Cl.
CPC ............ *C01C 1/0488* (2013.01); *C01B 3/025* (2013.01); *C01B 3/382* (2013.01); *C01B 3/48* (2013.01);

(Continued)

(58) Field of Classification Search
None
See application file for complete search history.

(56) References Cited

U.S. PATENT DOCUMENTS 3,598,527 A * 8/1971 Quartulli .................. C01B 3/36
                                                         252/373
4,690,812 A * 9/1987 Ranke ................... C07C 273/10
                                                         423/359

(Continued)

FOREIGN PATENT DOCUMENTS

| CN | 101830775 A | 9/2010 |
|---|---|---|
| DE | 10 2004 049774 A1 | 4/2006 |

(Continued)

*Primary Examiner* — Wayne Langel
(74) *Attorney, Agent, or Firm* — Blank Rome LLP

(57) ABSTRACT

A process for co-production of ammonia, urea and methanol from natural gas, comprising the steps of (a) producing a synthesis gas by simultaneous feeding natural gas to an autothermal reformer (ATR) and to a steam methane reformer (SMR), the two reformers running in parallel, (b) feeding air to an air separation unit (ASU), where the air is split into oxygen, which is fed to the ATR, and nitrogen, (c) subjecting the synthesis gas from the SMR to a water gas shift, (d) removing the carbon dioxide from the synthesis gas from step (c) and leading it to urea synthesis in a urea synthesis unit, (e) combining the hydrogen-rich gas from step (d) with the nitrogen from step (b), removing catalyst poisons from the gases and leading the gas mixture to ammonia synthesis in an ammonia synthesis unit, (f) optionally removing part of the carbon dioxide from the syngas from the ATR in step (a) and leading it to urea synthesis in a urea synthesis unit and (g) leading the syngas from step (f) to the methanol synthesis unit, wherein synthesis gas from step (a) may be led either from the ATR outlet to the SMR outlet upstream from the shift stage or the other way.

7 Claims, 1 Drawing Sheet

(51) Int. Cl.
*F25J 3/04* (2006.01)
*C01B 3/52* (2006.01)
*C07C 29/151* (2006.01)
*C01B 3/50* (2006.01)
*C07C 273/10* (2006.01)

(52) U.S. Cl.
CPC ............... *C01B 3/50* (2013.01); *C01B 3/52* (2013.01); *C07C 29/1518* (2013.01); *C07C 273/04* (2013.01); *C07C 273/10* (2013.01); *F25J 3/04539* (2013.01); *F25J 3/04587* (2013.01); *C01B 2203/0233* (2013.01); *C01B 2203/0244* (2013.01); *C01B 2203/0283* (2013.01); *C01B 2203/0415* (2013.01); *C01B 2203/0475* (2013.01); *C01B 2203/06* (2013.01); *C01B 2203/061* (2013.01); *C01B 2203/068* (2013.01); *C01B 2203/1241* (2013.01); *C01B 2203/141* (2013.01); *C01B 2203/145* (2013.01); *Y02P 20/152* (2015.11); *Y02P 20/52* (2015.11)

(56) References Cited

U.S. PATENT DOCUMENTS

| | | | | |
|---|---|---|---|---|
| 5,523,483 A | * | 6/1996 | Singh | C01B 3/025 564/68 |
| 6,207,078 B1 | * | 3/2001 | Badano | C01B 3/025 252/373 |
| 7,521,483 B2 | * | 4/2009 | Davey | C01B 3/025 423/237 |
| 7,674,932 B2 | | 3/2010 | Davey et al. | |
| 2009/0105356 A1 | | 4/2009 | Bormann et al. | |
| 2011/0297886 A1 | * | 12/2011 | Panza | C01B 3/025 252/376 |

FOREIGN PATENT DOCUMENTS

| | | |
|---|---|---|
| GB | 2 407 819 A | 5/2005 |
| WO | WO 2011/020618 A1 | 2/2011 |
| WO | WO 2013/013895 A1 | 1/2013 |

\* cited by examiner

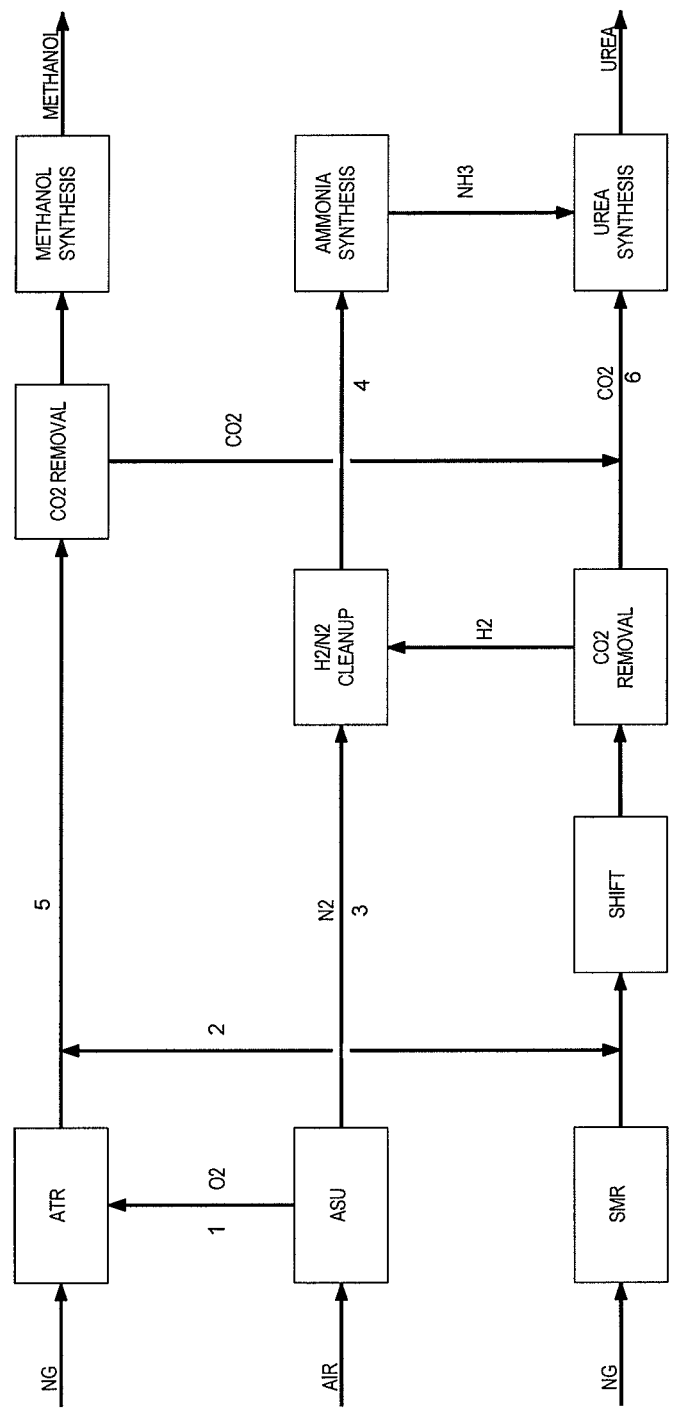

PROCESS FOR CO-PRODUCTION OF AMMONIA, UREA AND METHANOL

The present invention relates to a process for simultaneous production (co-production) of ammonia, urea and methanol, said process starting from the production of syngas. More specifically, the idea underlying the invention consists in using a combination of an ATR (auto-thermal reformer) and an SMR (steam methane reformer) front-end to make the required syngas for a range of combinations of ammonia, urea and methanol product.

Autothermal reforming is a technology commonly used for the production of syngas, where the conversion of a hydrocarbon feedstock, in this case natural gas, is carried out in a single reactor through the combination of partial combustion and adiabatic steam reforming. Combustion of the hydrocarbon feed is carried out with sub-stoichiometric amounts of air, enriched air or oxygen by flame reactions in a burner combustion zone. Steam reforming of the partially combusted hydrogen feedstock is subsequently conducted in a fixed bed of a steam reforming catalyst.

In the steam reforming process, syngas is produced from hydrocarbon feedstock by the reactions:

$$C_nH_m + H_2O \rightarrow nCO + (n+m/2)H_2 \quad (1)$$

$$CO + H_2O \rightarrow CO_2 + H_2 \quad (2)$$

$$CH_4 + H_2O \rightarrow CO + 3H_2 \quad (3)$$

The reactions are carried out in an externally heated reactor, the steam methane reformer (SMR), which is a primary reformer. The feed to the primary reformer may be desulfurized hydrocarbon feed mixed with steam or the partly converted product gas from a previous prereforming step. The primary reformer often is a fired tubular reformer consisting of catalyst-filled tubes placed in a furnace heated by one or more burners. It operates under conditions where the outlet temperature from the catalyst-filled tubes is relatively high, usually in the range from 650 to 950° C.

In autothermal reforming the above steam reforming reactions (1)-(3) are supplemented with a partial combustion, which may be represented by the reaction:

$$CH_4 + \tfrac{1}{2}O_2 \rightarrow CO + 2H_2 \quad (4)$$

Applicant's published application WO 2013/013895 A1 describes a flexible process for the production of synthesis gas (syngas) from a hydrocarbon feedstock. Said process is particularly suitable for large methanol, ammonia and liquid hydrocarbon plants. The synthesis gas is produced in two single line steam reforming steps. The process according to the published application can be used for synthesis of ammonia, methanol, dimethyl ether (DME), liquid hydrocarbons and combinations thereof.

Various processes for co-production of ammonia and urea and of methanol and ammonia are known. Thus, a process for combined production of ammonia and urea via carbamate synthesis is known from US 2001/0002245 A1, and a method for the simultaneous modernization of a plant for ammonia production and a plant for urea production, likewise via carbamate synthesis, is known from EP 1 041 038 B1. A gasification process for co-production of ammonia and urea, in which two parallel gasifiers are utilized so as to optimize the $H_2/CO_2$ ratio in the combined syngas product, thereby maximizing the ammonia and urea production, is known from U.S. Pat. No. 6,448,441 B1.

US 2008/0207948 A1 discloses a method for the production of urea from natural gas, wherein natural gas undergoes partial oxidation or autothermal reforming with a gas containing oxygen in a first step, and the resulting raw synthesis gas, consisting essentially of CO, $CO_2$, $CH_4$ and $H_2$, can be transformed by catalytic conversion of CO and $H_2O$ to form $CO_2$ and $H_2$, whereupon CO and $CH_4$ are removed in a multistep gas cleaning process and hydrogen is converted to ammonia upon addition of nitrogen. The ammonia is subsequently recombined with the previously separated $CO_2$ in a second step, whereby the ammonia is fully converted to urea.

A process for production of ammonia and urea is described in WO 2012/126673 A1, where liquid ammonia produced in an ammonia section is fed to a urea section directly at the ammonia synthesis pressure, and where the liquid ammonia is purified at a high pressure by cooling, separating a gaseous fraction comprising hydrogen and nitrogen from the cooled liquid ammonia at a high pressure and reheating the liquid ammonia after separation of the gaseous fraction, thereby obtaining a reheated purified ammonia with a temperature, which is suitable for feeding to the urea synthesis process.

US 2012/0148472 A1 describes a process for co-producing methanol and ammonia, wherein a syngas mixture consisting essentially of carbon monoxide, carbon dioxide and hydrogen is first partially reacted in a methanol once-through reactor, unreacted syngas is divided into a first and a second stream, the first stream is purified and fed to an ammonia synthesis section, and the second stream is fed to a methanol synthesis and purification section. The process enables production of methanol and ammonia in an integrated single process starting from natural gas and air, and a balanced production of ammonia and carbon dioxide further allows a co-production of urea to be integrated.

Finally, US 2007/0299144 describes a method for co-producing methanol and ammonia from natural gas in a multistage process, whereby natural gas, steam and oxygen are mixed in a first reactor, in which the natural gas is partially oxidized and additionally reformed catalytically. The gas mixture from the first reactor is divided into a stream for methanol synthesis and another stream for hydrogen production. The CO present in the stream for hydrogen production is converted catalytically to $CO_2$ in another reactor with intermediate cooling, and remaining impurities such as methane, traces of CO and argon are washed out. The $CO_2$ is branched off for urea synthesis. The methanol synthesis gas is converted catalytically to methanol, which is brought to the required purity by distillation, and the ammonia synthesis gas is compressed and converted catalytically to ammonia, which is separated from the recovered synthesis gas by partial condensation.

The above-mentioned published application WO 2013/013895 A1 belonging to the applicant describes a combined parallel SMR and ATR reforming scheme for the preparation of syngas, which can be further converted and/or purified as required for production of hydrogen, carbon monoxide, mixtures of hydrogen and carbon monoxide, as well as for the production of methanol, ammonia, dimethyl ether (DME) and liquid hydrocarbons. The present invention is a further development of the process scheme described in the published application. This invention relates to integration of nitrogen from an air separation unit (ASU) and $CO_2$ optimisation for co-producing ammonia, urea and methanol.

More specifically, the present invention relates to a process for co-production of ammonia, urea and methanol from natural gas, comprising the steps of:

(a) producing a synthesis gas by simultaneous feeding natural gas to an autothermal reformer (ATR) and to a steam methane reformer (SMR), the two reformers running in parallel;
(b) feeding air to an air separation unit (ASU), where the air is split into oxygen, which is fed to the ATR, and nitrogen;
(c) subjecting the synthesis gas from the SMR to a water gas shift;
(d) removing the carbon dioxide from the synthesis gas from step (c) and leading it to urea synthesis in a urea synthesis unit;
(e) combining the hydrogen-rich gas from step (d) with the nitrogen from step (b), removing catalyst poisons and part of inerts from the gases and leading the gas mixture to ammonia synthesis in an ammonia synthesis unit;
(f) removing part of the carbon dioxide from the syngas from the ATR in step (a) and leading it to urea synthesis in a urea synthesis unit; and
(g) leading the syngas from step (f) to the methanol synthesis unit, wherein synthesis gas from step (a) may be led either from the ATR outlet to the SMR outlet upstream from the shift stage or the other way.

The combined use of an SMR and an ATR running in parallel makes it possible to produce both ammonia, which can be further converted to urea, and methanol in the same plant with optimal use of the $CO_2$. Since ammonia, urea and methanol are all desired products, the air separation unit (ASU) is fully utilized, because the oxygen goes to the methanol part of the plant, while the nitrogen goes to the ammonia part of the plant. Using this combination of an ATR and an SMR makes it possible to make the required syngas for a range of different combinations of the products ammonia, urea and methanol. By using an ATR the overall costs can be reduced, and it further becomes possible to build larger capacity co-production units compared to having only an SMR front-end.

When urea is produced from natural gas using an SMR front-end, this typically leads to a $CO_2$ deficit requiring excess reforming. In the process according to the invention a $CO_2$ deficient gas from the SMR is mixed with a $CO_2$ rich gas from the ATR, which provides a means to optimize the $CO_2$ balance.

The sole figure of the Drawings illustrates the process of the invention.

Referring to the figure, natural gas (NG) is fed to each of the two reformers, i.e. the autothermal reformer (ATR) and the steam methane reformer (SMR). Simultaneously, air is fed to an air separation unit (ASU), in which air is separated into $O_2$, which is led to the ATR via line 1, and $N_2$, which is led forward via line 3 as nitrogen source to the $NH_3$ synthesis. The hydrogen that remains after removal of $CO_2$ is to be passed through either a methanator, before it is mixed with the nitrogen from the ASU, or a nitrogen wash. In both cases the resulting mixture of $N_2$ and $H_2$ is sent to the $NH_3$ synthesis via line 4.

Part of the syngas produced in the ATR is fed via line 5 to a $CO_2$ removal unit and from there to methanol synthesis. The remainder of said syngas can be passed to the inlet shift via line 2 as shown in the FIGURE, but the passage can also be reversed, i.e. from the SMR to the methanol synthesis.

The removal of carbon dioxide from the synthesis gas from step (c) may be performed by any conventional means in a physical or chemical wash as known in the art. Preferably carbon dioxide is removed by any process known per se which allows for easy recovery of absorbed carbon dioxide for use in urea synthesis.

The carbon dioxide separated from the synthesis gas above is mixed with the carbon dioxide removed after the shift, and the resulting gas is passed via line 6 to the urea synthesis.

The combining of the hydrogen-rich gas from step (d) with the nitrogen from step (b) is performed as an $H_2/N_2$ cleanup, where carbon monoxide is converted to methane in at least one methanation reactor, preferably an adiabatic reactor containing a fixed bed of a methanation catalyst.

The ammonia synthesis gas from the methanation stage, which contains the correct proportion of hydrogen and nitrogen ($H_2:N_2$ molar ratio of 3:1), is optionally passed through a compressor (not shown) in order to obtain the required ammonia synthesis pressure, such as 120 to 200 bar, preferably about 130 bar. Ammonia is then produced in a conventional manner by means of an ammonia synthesis loop comprising at least one ammonia converter containing at least one fixed bed of ammonia catalyst, with inter-bed cooling. Ammonia may be recovered from the effluent containing ammonia as liquid ammonia by condensation and subsequent separation. Preferably, an off-gas stream containing hydrogen, nitrogen and methane is withdrawn from the ammonia synthesis stage, as is also a hydrogen-rich stream (>90 vol % $H_2$). These streams may for instance stem from a purge gas recovery unit.

The required steam-to-carbon ratio (S/C ratio), defined as the molar ratio between the total amount of steam added to the process in the steam reforming step and the carbon contained in the hydrocarbon feed, depends on the particular steam reforming technique. Typical S/C values for syngas preparation are >0.4 for ATR and >1.4 for SMR, respectively. By using ATR in the combined plant according to the invention it is possible to operate with an overall lower S/C ratio, which is an advantage, because it enables construction savings of 10 to 15%. Using $N_2$ from the ASU as $N_2$ source for the $NH_3$ synthesis as mentioned above will give a further construction saving in the gas preparation and cooling sections because $N_2$ is not passed through these.

In the process according to the present invention, the syngas from the ATR has an S/C ratio of between 0.4 and 1.8, and it is preferably around 0.6. The syngas from the SMR has an S/C ratio of between 1.4 and 3.3, preferably around 2.5.

The invention allows optimal $CO_2$ management for producing the full range of product combinations of methanol and urea.

If more methanol is required, SMR syngas is directed to the methanol synthesis.
If more urea is required, ATR syngas is directed to the shift downstream the ATR, and $CO_2$ is optionally removed from the synthesis gas feed to the methanol synthesis and used for urea production.

The invention can also be used to produce liquid ammonia in combination with methanol and urea. In this case the invention will help to reduce or in some cases even avoid excess process $CO_2$.

The invention is described in greater detail in the following example by reference to the FIGURE, which illustrates the concept of the invention.

EXAMPLE

The conditions for an ATR reforming section and an SMR reforming section are listed in Table 1. Pure methane is used as feed in the example, but it can be any typical hydrocarbon feed. The result for a natural gas containing higher hydrocarbons and/or $CO_2$ will result in a relatively larger SMR section compared to the ATR section than used in the example.

Table 1 below lists the dry gas composition of the synthesis gases, the oxygen consumption and the available nitrogen.

The dry gas compositions show the difference in hydrogen and carbon composition making it possible to optimise the $CO_2$ management such that the overall process can be made without excess $CO_2$.

TABLE 1

| Reforming step | ATR | SMR |
|---|---|---|
| flow, $Nm^3/h$ | 160000 | 21000 |
| steam/carbon, S/C | 0.6 | 2.5 |
| $CH_4$, mole % | 100 | 100 |
| syngas, $Nm^3/h$ | 470000 | 80850 |
| $H_2$, mole % | 66 | 74 |
| CO, mole % | 27.5 | 16.5 |
| $CO_2$, mole % | 5 | 6 |
| $CH_4$, mole % | 1.5 | 3.5 |
| oxygen, $Nm^3/h$ | 78000 | |
| nitrogen, $Nm^3/h$ | 300000 | |

It is clear that even if all the synthesis gas is used to make urea, there will be an excess of nitrogen.

In Table 2 below, the results of various product scenarios are calculated. A common feature for all cases is that all process $CO_2$ is used for producing urea and/or methanol. The table illustrates that the concept allows any product split between urea and methanol without excess $CO_2$ from the process.

TABLE 2

| ATR, $CH_4$ flow 1000 $Nm^3/h$ | 160 | 160 | 160 | 160 | 160 | 100 | 100 |
|---|---|---|---|---|---|---|---|
| SMR, $CH_4$ flow 1000 $Nm^3/h$ | 23 | 22 | 21 | 21 | 21 | 20 | 40 |
| % SMR syngas to urea | 100 | 100 | 100 | 100 | 100 | 0 | 50 |
| % ATR syngas to urea | 100 | 75 | 50 | 25 | 0 | 0 | 0 |
| MeOH, MTPD* | 0 | 1200 | 2400 | 3600 | 4800 | 3700 | 3700 |
| Urea, MTPD* | 11100 | 8700 | 6300 | 3900 | 1500 | 0 | 1100 |

*MTPD = metric tons per day

The invention claimed is:

1. A process for co-production of ammonia, urea and methanol from natural gas, comprising the steps of:
   (a) producing a synthesis gas by simultaneous feeding natural gas to an autothermal reformer (ATR) and to a steam methane reformer (SMR), the two reformers running in parallel;
   (b) feeding air to an air separation unit (ASU), where the air is split into oxygen, which is fed to the ATR, and nitrogen;
   (c) subjecting the synthesis gas from the SMR to a water gas shift stage to form a $CO_2$ rich gas;
   (d) removing carbon dioxide from the synthesis gas from step (c) and producing a hydrogen-rich gas and removed $CO_2$, and leading the removed $CO_2$ to urea synthesis in a urea synthesis unit;
   (e) combining the hydrogen-rich gas from step (d) with the nitrogen from step (b) to form a mixed gas, and removing catalyst poisons and part of inerts from the mixed gas to form an ammonia feed, and leading the ammonia feed to an ammonia synthesis in an ammonia synthesis unit;
   (f) removing part of carbon dioxide from the syngas from the ATR in step (a) and leading the $CO_2$ removed from the ATR to the urea synthesis unit; and
   (g) leading $CO_2$ reduced syngas from step (f) to a methanol synthesis unit,
   wherein a part of the synthesis gas from the ATR of step (a) is led to the SMR outlet upstream from the shift stage or part of the synthesis gas from the SMR from step (a) is combined with the syngas from the ATR.

2. The process according to claim 1, wherein the syngas from the ATR has a steam-to-carbon ratio (S/C ratio) of between 0.4 and 1.8.

3. The process according to claim 1, wherein the syngas from the SMR has an S/C ratio of between 1.4 and 3.3.

4. The process according to claim 1, wherein syngas from the SMR is sent to the methanol synthesis unit to increase methanol production.

5. The process according to claim 1, wherein $CO_2$ present in the syngas from the ATR is optionally removed upstream of the methanol synthesis unit and fed to the urea synthesis stage.

6. The process according to claim 1, wherein SMR syngas is directed to the methanol synthesis, to obtain higher proportions of methanol.

7. The process according to claim 1, wherein ATR syngas is directed to the shift downstream the ATR, and $CO_2$ is removed from the synthesis gas fed to the methanol synthesis unit and used for urea production to provide a higher proportion of urea.

* * * * *